United States Patent
Derking et al.

(10) Patent No.: US 7,863,493 B2
(45) Date of Patent: Jan. 4, 2011

(54) PROCESS FOR PREPARING AN ORGANIC HYDROPEROXIDE, INDUSTRIAL SET-UP THEREFORE AND PROCESS WHEREIN SUCH ORGANIC HYDROPEROXIDE IS USED IN THE PREPARATION OF AN ALKYLENE OXIDE

(75) Inventors: Anke Derking, Amsterdam (NL); Wan Shi Foong, Jurong Island (SG); Raymond Lawrence June, Jurong Island (SG); Chao-Yuan Kho, Singapore (SG); Mohammad Azmi Bin Othman, Amsterdam (NL); Hoi-Yan Yuen, Jurong Island (SG)

(73) Assignee: Shell Oil Company, Houston, TX (US)

( * ) Notice: Subject to any disclaimer, the term of this patent is extended or adjusted under 35 U.S.C. 154(b) by 1103 days.

(21) Appl. No.: 11/425,660

(22) Filed: Jun. 21, 2006

(65) Prior Publication Data

US 2007/0282146 A1 Dec. 6, 2007

(30) Foreign Application Priority Data

Apr. 12, 2006 (SG) .............................. 200602449-1

(51) Int. Cl.
*C07C 15/46* (2006.01)
(52) U.S. Cl. ...................... 585/438; 568/576; 568/959
(58) Field of Classification Search ...................... None
See application file for complete search history.

(56) References Cited

U.S. PATENT DOCUMENTS

| | | | | |
|---|---|---|---|---|
| 5,883,268 | A | 3/1999 | Lin et al. ..................... | 549/529 |
| 6,465,695 | B1 * | 10/2002 | Fulmer et al. ................ | 568/571 |
| 6,512,129 | B1 | 1/2003 | Li et al. ........................ | 549/529 |
| 6,620,974 | B2 * | 9/2003 | Fulmer et al. ................ | 568/571 |
| 6,700,005 | B2 * | 3/2004 | Kremers et al. .............. | 549/529 |
| 6,700,024 | B2 * | 3/2004 | Du Cauze de Nazelle et al. ............................ | 568/571 |
| 6,974,888 | B2 * | 12/2005 | Kremers et al. .............. | 585/435 |
| 2004/0210069 | A1 * | 10/2004 | Foong et al. ................. | 549/529 |
| 2005/0215802 | A1 * | 9/2005 | Heiszwolf et al. ........... | 549/529 |

FOREIGN PATENT DOCUMENTS

| | | |
|---|---|---|
| DE | 19903114 | 8/2000 |
| EP | 345856 | 12/1989 |
| GB | 1251042 | 1/1969 |
| WO | 99/42425 | 8/1999 |
| WO | 99/42426 | 8/1999 |
| WO | WO02051801 | 7/2002 |
| WO | WO03024925 | 3/2003 |
| WO | 03/066584 | 8/2003 |
| WO | WO03066584 | 8/2003 |
| WO | WO2004076408 | 9/2004 |
| WO | WO2005075444 | 8/2005 |
| WO | WO2005092468 | 10/2005 |

OTHER PUBLICATIONS

"New Fundamentals for Liquid-Liquid Dispersion Using Static Mixers", Mixing IX, 1997 by Streiff et al.
"Finest Drop Coalescer Elements Promote Product Recovery," Filtration and Separation, Croydon, GB, vol. 40, No. 4, May 2003 pp. 22-25.

* cited by examiner

*Primary Examiner*—Daniel M Sullivan
*Assistant Examiner*—Chukwuma O Nwaonicha

(57) ABSTRACT

A process for preparing an organic hydroperoxide, which process comprises:
(a) oxidizing an organic compound to obtain an organic reaction product containing organic hydroperoxide;
(b) mixing at least part of the organic reaction product of step (a) with a basic aqueous solution to obtain a mixture of basic aqueous solution and the organic reaction product;
(c) separating the mixture of step (b) to obtain a separated organic phase containing organic hydroperoxide, and a separated aqueous phase;
(d) mixing at least part of the separated organic phase of step (c) with water to obtain a mixture of an aqueous phase and the organic phase; and
(e) separating the mixture of step (d) to obtain a separated organic phase containing organic hydroperoxide, and a separated aqueous phase; in which process the separation to a separated organic phase and a separated aqueous phase in step (e) is carried out with the help of a coalescer containing glass fibers.

6 Claims, 2 Drawing Sheets

US 7,863,493 B2

PROCESS FOR PREPARING AN ORGANIC HYDROPEROXIDE, INDUSTRIAL SET-UP THEREFORE AND PROCESS WHEREIN SUCH ORGANIC HYDROPEROXIDE IS USED IN THE PREPARATION OF AN ALKYLENE OXIDE

This application claims the benefit of Singapore Application 200602449-1 filed Apr. 12, 2006.

FIELD OF THE INVENTION

The present invention relates to a process for preparing an organic hydroperoxide, an industrial set-up therefore and a process wherein such organic hydroperoxide is used for the preparation of an alkylene oxide.

BACKGROUND OF THE INVENTION

U.S. Pat. No. 5,883,268 describes a process for preparing propylene oxide that comprises peroxidation of ethylbenzene. The peroxidation reaction mixture can be contacted with aqueous base in an amount sufficient to neutralize acidic components. Subsequently the resulting mixture can be phase separated into separate aqueous and organic (hydrocarbonaceous) phases. The organic phase, which contains some base, can be water washed to separate the basic materials. In the process of U.S. Pat. No. 5,883,268 water was stripped from the organic phase.

WO-A-03/066584 describes a process for preparing alkylaryl hydroperoxide containing product. In this process an aqueous phase also has to be separated from an hydrocarbonaceous phase. The separation in WO-A-03/066584 can partly be carried out with the help of a coalescer.

The presence of residual basic materials, such as sodium salts, in an organic phase comprising an organic hydroperoxide may cause problems in subsequent processing of the organic hydroperoxide.

Improvement of the removal of such basic materials, furthermore allows higher amounts of base to be used for neutralizing any acidic components in the peroxidation reaction mixture. By improvement of the efficiency of the basic material removal, the removal of acidic components can therefore also be improved.

It is thus desirable to provide an improved process for the preparation of an organic hydroperoxide, wherein the removal of basic materials can be improved.

SUMMARY OF THE INVENTION

It has now been found that the removal of the basic materials can be improved by separating the aqueous phase and the organic phase with help of a coalescer containing glass fibers. Surprisingly the glass fibers are found to function well in the hostile environment of the process according to the invention and little corrosion is observed. Accordingly, the present invention provides a process for preparing an organic hydroperoxide, which process comprises:
(a) oxidizing an organic compound to obtain an organic reaction product containing organic hydroperoxide;
(b) mixing at least part of the organic reaction product of step (a) with a basic aqueous solution to obtain a mixture of basic aqueous solution and the organic reaction product;
(c) separating the mixture of step (b) to obtain a separated organic phase, containing organic hydroperoxide, and a separated aqueous phase;
(d) mixing at least part of the separated organic phase of step (c) with water to obtain a mixture of an aqueous phase and the organic phase; and
(e) separating the mixture of step (d) to obtain a separated organic phase, containing organic hydroperoxide, and a separated aqueous phase;

in which process the separation to a separated organic phase and a separated aqueous phase in step (e) is carried out with the help of a coalescer containing glass fibers.

Glass fibers are generally not used in processes in which they are brought in contact with strongly basic or acidic compounds in view of possible corrosion of the fibers. This makes it very surprising that glass fibers perform well in the present process.

In addition the use of glass fibers makes it possible to limit the time and space necessary for the organic phase and the aqueous phase to settle. In the past such separation of the organic phase and the aqueous phase required a set-up including a separate settling vessel followed by a separation vessel including possible coalescing means. The present invention makes it possible to use only a separation vessel, comprising coalescing means and a settling zone, such that no separate preceding settling vessel is needed before entering the separation vessel.

The organic hydroperoxide provided by the process according to the invention can advantageously be used in a process for preparing an alkylene oxide, which process comprises preparing an organic phase, containing organic hydroperoxide according to the above process and a further step of contacting at least part of the obtained organic phase, containing organic hydroperoxide, with an alkene to obtain an alkylene oxide and an organic alcohol.

In addition to the above, the present invention further provides an industrial set-up for removing basic materials from an organic phase containing organic hydroperoxide, which set-up comprises a mixer for mixing the organic phase with water; and a separation vessel connected directly or indirectly to the mixer for separating the obtained mixture into a purified organic phase, containing organic hydroperoxide, and an aqueous phase;

wherein the mixer is a static mixer and the separation vessel comprises one or more coalescers containing glass fibres.

BRIEF DESCRIPTION OF THE DRAWINGS

The invention is illustrated by the following figures.

DETAILED DESCRIPTION OF THE INVENTION

Figure 1:
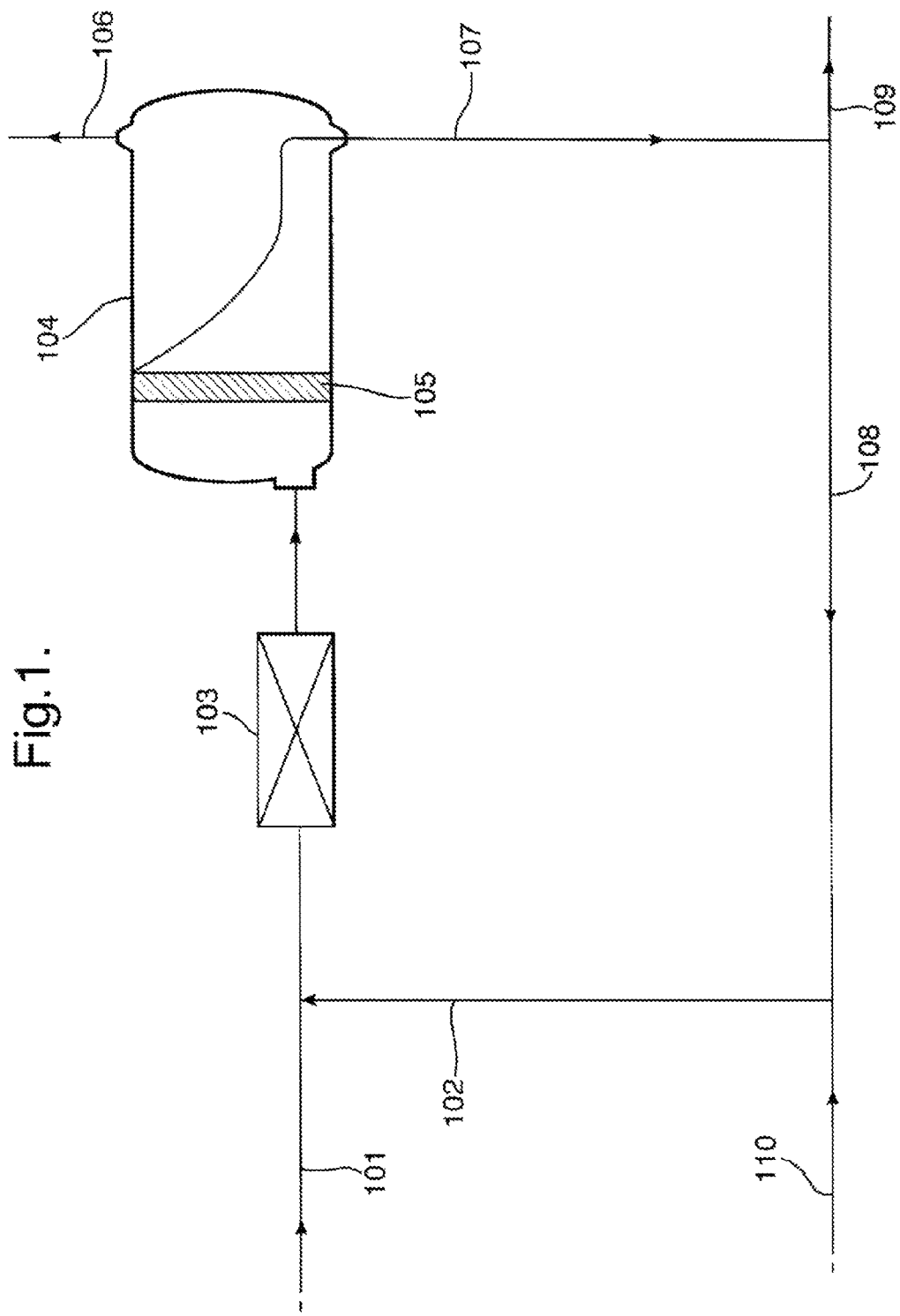
FIG. 1 is a schematic illustration of an industrial set up for a method according to the invention.

The organic compound used in the process of the present invention can in principle be any compound. Examples of suitable organic compounds include alkylaryl compounds and tertiary alkyl compounds. Alkylaryl compounds which are most frequently used are benzene compounds containing at least 1 alkyl substituent which alkyl substituent contains from 1 to 10 carbon atoms, preferably from 2 to 8 carbon atoms. Preferably, the benzene compound contains an average of 1 to 2 constituents. More preferred alkylaryl compounds are ethylbenzene, cumene and di(iso-propyl)benzene. Tertiary alkyl compounds that can be used include tertiary butane (i.e. 2-methyl propane). Most preferably the organic compound is ethylbenzene. When ethylbenzene is used as the organic compound, the process can be used to prepare ethylbenzene hydroperoxide.

The oxidation of the organic compound in step a) of the process according to the invention can be carried out by any suitable process known in the art. The oxidation is preferably carried out by contacting the organic compound with an oxygen-containing gas, such as for example air. The oxidation can be carried out in the liquid phase in the presence of a diluent. This diluent is preferably a compound which is liquid under the reaction conditions and does not react with the starting materials and product obtained. However, the diluent can also be a compound necessarily present during the reaction. For example, if the alkylaryl is ethylbenzene the diluent can be ethylbenzene as well. In a preferred embodiment the process can thus be used to prepare a solution of ethylbenzene hydroperoxide in ethylbenzene. In a further preferred embodiment the oxidation product is subsequently concentrated, for example by means of flashing.

Besides the desired organic hydroperoxide, a wide range of contaminants are created during the oxidation of organic compounds. Although most of these are present in small amounts, the presence of organic acids has been found to sometimes cause problems in the further use of the organic hydroperoxides. As described in U.S. Pat. No. 5,883,268, a method of reducing the amount of contaminants comprises contacting the reaction product containing organic hydroperoxide with an aqueous alkali metal solution (i.e. an aqueous base). However, contact with the aqueous alkali metal solution introduces a certain amount of alkali metal into the organic hydroperoxide containing reaction product. Although the amount of organic acids can be decreased by the alkali metal wash, the amount of alkali metal contaminants is increased.

In step (b) of the process of the present invention, at least part of the organic reaction product, which product contains organic hydroperoxide, is mixed with a basic aqueous solution to obtain a mixture. As a result at least part of the organic acid byproducts can be neutralized. Preferably, essentially all of the organic reaction product is mixed with a basic aqueous solution.

By mixing is understood that the organic reaction product and the basic aqueous solution are contacted with each other in such a manner that a mixture of the two is obtained. By mixing, a large interfacial area can be created between the organic reaction product and the aqueous solution, which allows mass transfer. The mixing in step (b) can be carried out in any manner known to the skilled person to be suitable for such a process, including for example by means of a static mixer, a stirred tank or by means of fibrous contacting devices.

Preferably a basic aqueous solution containing one or more alkali metal compounds is used. Suitable alkali sources for use in the aqueous alkali metal solution include alkali metal hydroxides, alkali metal carbonates and alkali metal hydrogen carbonates. Examples of these compounds are NaOH, KOH, $Na_2CO_3$, $K_2CO_3$, $NaHCO_3$ and $KHCO_3$. In view of their easy availability, it is preferred to use NaOH and/or $Na_2CO_3$. The amount of alkali metal present in the aqueous alkali metal solution may vary widely. Preferably concentrations of 0.01 to 25% w/w of alkali metal and more preferably concentrations of 0.1 to 10% w/w of alkali metal based on the total aqueous solution are used.

In a preferred embodiment, step (b) comprises dispersing the basic aqueous solution into at least part of the organic reaction product, such that the mixture obtained is a dispersion of droplets of basic aqueous solution in an organic phase.

In step (c) the mixture obtained in step b) is separated into an organic phase, containing organic hydroperoxide, and an aqueous phase. The separation can be carried out in any manner known to the person skilled in the art. Preferably the separation is carried out by phase separation, for example by using settling vessels.

In step (d), at least part of the separated organic phase of the previous step is washed with water. More preferably essentially all of the organic phase obtained in the previous step is washed with water. The water can be clean water but preferably consists at least partly of waste water. The washing will generally be carried out with the help of a combination of fresh water, recycle water and optionally further waste water obtained in other steps of the present process.

This washing is carried out by mixing at least part of the organic phase with water to obtain a mixture of an aqueous phase and the organic phase in step (d).

By mixing is understood that the organic phase of step (c) and the water are contacted with each other in such a manner that a mixture of the two is obtained.

In a preferred embodiment, step (d) comprises dispersing the water into at least part of the organic phase obtained in step (c), such that the mixture obtained as a dispersion of droplets of water in an organic phase.

The mixture of the organic phase and the aqueous phase obtained in step (d) is separated again in step (e).

Dependent on the amount of contaminants present in the organic phase containing organic peroxide, the combination of process step (d) and (e) can either be carried out once or a number of times. In a preferred embodiment the sequence of steps (d) and (e) is repeated one or more times. If repeated, steps (d) and (e) are preferably repeated once or twice, making a total of two or three washing steps (d) and separation steps (e).

According to the invention at least one of the steps (e) is carried out with the help of a coalescer containing glass fibers. Preferably all steps (e) present in the process are carried out with the help of a coalescer containing glass fibers.

Preferably, a step (d) preceding a step (e) wherein a coalescer containing glass fibers is used, is carried out at a specific volume ratio. When step (e) is carried out with the help of a coalescer containing glass fibers, the volume ratio of aqueous phase to organic phase in step (d) lies preferably in the range from 1:100 to 1:2. More preferably the volume ratio in such a step (d) lies in the range from 1:10 to 1:3, most preferably in the range from 1:8 to 1:4.

The mixing in step (d) can be carried out in any manner known to the skilled person to be suitable for such a process, including for example by means of a static mixer, a stirred tank or by means of fibrous contacting devices. In a preferred embodiment, however, the organic phase and the aqueous phase are mixed in a controlled manner with sufficient turbulence. Preferably, therefore, the organic phase is contacted with the water in step (d) by means of a static mixer.

The mixing mechanism of a static mixer differs from the mechanisms in other types of mixers such as a stirred tank. Static mixers provide a longer contacting time between two phases at a high turbulence and as a result a more uniform droplet size distribution can be obtained with a static mixer than with a stirred tank. That is, the use of a static mixer results in better controllability of the mixture and the droplet size. The static mixer may be any static mixer known to the skilled person. Examples of suitable static mixers are for example described in "Mixing in the Process Industries" by N. Harnby et al. In a preferred embodiment the static mixer is operated in such a manner that a pressure drop over the static mixer exceeding 0.05, preferably exceeding 0.1 bar is obtained.

Preferably the static mixer contains in the range from 1 to 30 mixing elements, more preferably from 2 to 20 elements and most preferably from 3 to 12 elements. As illustrated by N. Harnby et al, a mixing element is generally a tube comprising obstacles, for example baffles, which cause discontinuous or continuous changes in the flow direction. The obstacles cause intense turbulence. For practical purposes the elements are preferably placed in a sequence such that the direction changes from element to element.

The diameter of the static mixer can vary widely. For practical purposes the diameter of the static mixer varies between 2 millimeters and 2 meters.

When preceding a step (e) wherein a coalescer containing glass fibers is used, step (d) preferably comprises mixing the organic phase and the water in such a manner and to such an extent that a specific droplet size is obtained. More preferably a dispersion is prepared in such a step (d) comprising droplets which have a Sauter mean droplet size in the range from 30 to 300 micrometers. More preferably the droplets have a Sauter mean droplet size in the range from 50 to 250 micrometers. The Sauter mean droplet size can be determined by the method as described in the article of Streiff et al. "New Fundamentals for Liquid-Liquid Dispersion Using Static Mixers", Mixing IX, 1997. The properties of the mixture, such as viscosity, surface tension, density and flow rate, are measured and subsequently the droplet size can be calculated with equation (9) mentioned in this article.

The droplets are preferably water droplets dispersed in the organic phase.

Droplets with the above mentioned mean droplet sizes can advantageously be obtained by using a static mixer.

In a preferred embodiment, step (e) comprises allowing the organic phase and aqueous phase to coalesce, e.g. by forming big droplets, in a coalescer and subsequently to allow the phases to separate in a settling zone. By using the coalescer the separation is accelerated. In such case, step (e) preferably comprises:

(1) treating the mixture obtained in step d) in a coalescer containing glass fibers to obtain a mixture comprising droplets with an increased droplet size;
(2) allowing the mixture comprising droplets with an increased droplet size, obtained in step (1), to settle in a settling zone to obtain a separated organic phase and a separated aqueous phase;
(3) removing the organic phase and the aqueous phase from the settling zone.

By increasing the droplet size through coalescence, a first (partial) phase separation can be obtained in step (1) allowing for an improved separation in step (2). The settling zone can be a separate settling vessel or a settling zone integrated in the same vessel as the coalescer. Preferably one separation vessel is used comprising both a coalescer and a settling zone.

In case of large volumes, the coalescer can advantageously be preceded by an additional settling zone. In such a case step e) comprises an additional settling step (0) wherein the mixture is allowed to settle in a settling zone into an organic phase and an aqueous phase, whereafter the two phases are separated. Preferably, the separated organic phase, still containing water droplets dispersed therein, is hereafter treated with the help of a coalescer containing glass fibers in step (1).

The use of such an additional settling step becomes especially advantageous as a higher volume ratio of aqueous phase to organic phase is used. It is especially advantageous when the volume ratio of aqueous phase to organic phase in step (d) lies in the range from 1:8 to 1:4.

The glass fiber to be applied in the present invention can be any glass fiber. Preferably, however, the glass fiber is free of phosphorus and/or sulphur containing additives. It was found that in some cases, these additives could lead to increased decomposition of the organic hydroperoxide. Preferred glass fibers are fibers made from glass containing less than 1000 ppmw of elemental sulphur, based on total amount of glass. The amount of elemental phosphorus, based on total amount of glass, is preferably at most 1000 ppmw. Most preferably the amount of elemental sulphur is at most 290 ppmw while additionally the amount of elemental phosphorus is at most 250 ppmw.

Any type of glass fibers known to the skilled person can be used. Examples of suitable glass types include A-type glass (i.e. soda lime silicate glasses), C-type glass (i.e. Calcium borosilicate glasses), D-type glass (i.e. Borosilicate glasses with a low dielectric constant), E-type glass (i.e. Alumina-calcium-borosilicate glasses with a maximum alkali content of 2% w/w), ECRGLASS® (i.e. a calcium aluminosilicate glass), AR-type glass (i.e. alkali-resistant glasses composed of alkali zirconium silicates), R-type glass (i.e. calcium aluminosilicate glasses) and S-2-type glass (i.e. magnesium aluminosilicate glasses). Of these, C-type glass, ECRGLASS® and R-type glass are preferred because of their acid corrosion resistance and AR glass is especially preferred because of its alkali resistance. In another advantageous embodiment, E-type glass was used. It was advantageously found that when E-type glass was used surprisingly little corrosion of the glass occurred. This has been illustrated by the figures of the examples.

The thickness of the glass fibers can vary widely. Preferably, however, the diameter of the glass fibers lies in the range from 0.1 to 50 micrometers. More preferably the diameter of the glass fibers lies in the range from 1 to 20 micrometers and even more preferably in the range from 5 to 15 micrometers.

In a preferred embodiment, the glass fibres can be co-knitted with other materials, such as for example stainless steel or Teflon fibres. The use of such a co-knit, with for example stainless steel or Teflon material, is advantageous as the Teflon or stainless steel will support the glass fibers and prevents the glass fibers from compacting under the pressure of the flow. Especially preferred is a combination of fine glass fibers, for example having a diameter in the range from 1 to 20 microns, in combination with more coarse Teflon fibres, for example having a diameter in the range from 20 to 40 microns, or stainless steel fibers, for example having a diameter in the range form 250 to 300 microns.

If desired, combinations of beds of different materials can also be used. For example one or more beds consisting of glass fibres can be combined with one or more beds of another material or a co-knit of materials.

By a coalescer is understood a means to assist in the coalescence of a first phase mixed into another phase. More specifically, a coalescer can be understood to be a means in which a dispersion is forced through a coalescing medium, used for the coalescence and separation of finely dispersed droplets. The coalescing medium may be understood to work by holding up the dispersed droplets long enough for them to form droplets of sufficient size to settle. In the process according to the invention the glass fibers may be understood to be such a coalescing medium.

The coalescer can for example be present in the form of a coalescer cartridge, i.e. a container holding fibers in a specific arrangement. In another example the coalescer can be present in the form of a coalescer bed, i.e. a knitted, woven or pressed "fabric" of fibers, which is fixed into a separation vessel, sometimes also referred to as a coalescer mat.

The coalescer for use in the present invention can be any coalescer known to be suitable to someone skilled in the art.

The coalescer will often be placed within a separation vessel, i.e. a vessel in which the separation of the aqueous phase and the organic phase can be carried out. Separation vessels in which the coalescer can be used include vertical or horizontal vessels. Preferably a horizontal separation vessel is used.

One separation vessel can comprise one or more coalescers. Preferably one separation vessel comprises from 1 to 10, more preferably from 1 to 5 coalescers.

Such coalescers can be located in such a separation vessel in any manner known to the skilled person. For example, such coalescers can be located horizontally, diagonally or vertically in the separation vessel. In one preferred embodiment the coalescers are located essentially vertically, whilst the mixture of organic and aqueous phase flows through the coalescers in an essentially horizontal direction through an essentially horizontal separation vessel. In another preferred embodiment the coalescers are located essentially horizontally, whilst the mixture of organic and aqueous phase flows through the coalescers in an essentially vertical direction through an essentially vertical separation vessel.

The coalescers can be located at any place within the separation vessel, for example at the upper half of a horizontal separation vessel; over the whole length of a horizontal separation vessel; or in the lower half of a horizontal separation vessel. In a preferred embodiment at least one coalescer is placed essentially vertically over the full length of an essentially horizontal separation vessel. In an especially preferred embodiment the separation vessel is an essentially horizontal separation vessel comprising one or two coalescers over the full cross-section of the separation vessel located in an essentially vertical manner in the upstream half of the separation vessel; and further comprising one or two coalescers over part of the cross-section of the separation vessel, located in an essentially vertical manner in the downstream half of the separation vessel. The coalescers located in the downstream half of the separation vessel preferably extend from the top of the separation vessel to less than $9/10$, preferably less than $4/5$, and more preferably less than $2/3$ of the height of the separation vessel, leaving a passage open on the bottom of the separation vessel.

The separation vessels can contain a coalescer in for example the form of a coalescer mat or a coalescer cartridge. The use of cartridges can be advantageous if a larger contact area is desired. A larger contact area allows lower space velocities.

Examples of suitable coalescers are for example described in "Liquid-Liquid coalescer Design Manual" of ACS Industries, LP, Houston, Tex., USA.

One or more coalescer mats or cartridges can be used in a separation vessel. For example, a separation vessel can comprise a combination of a first and second coalescer mats connected to each other in the front of the separation vessel and a combination of a third and a fourth coalescer mats connected to each other at a second location more downstream in the vessel.

As indicated above, the coalescer mats and/or cartridges can be applied in a horizontal or vertical manner.

If desirable, the mixture of organic and aqueous phases can be filtered through a filter before contact with the glass fibers. Such filters generally have openings of at most 20 micrometers, preferably of at most 10 micrometers.

The coalescer for use in the present invention, can be used in the conventional way as is known to those skilled in the art. It is customary to monitor the pressure drop over a coalescer during operation. If the pressure drop has become unacceptable, the coalescer can be cleaned for example by backwashing.

The separation of organic phase and aqueous phase in step (e) is preferably carried out in a continuous manner. Preferably the mixture obtained in step (d) is fed to a separation vessel in step (e) at a velocity in the range from 0.01 to 10.0 cm/s, more preferably in the range from 0.1 to 3.0 cm/s.

The pressure used during the separation can vary widely. The separation is preferably carried out in the liquid phase preferably at a pressure in the range from 0.01 to 80 bar, more preferably in a range from 0.1 to 17 bar. Preferably, the separation of organic phase and aqueous phase in step (e) is carried out at a temperature of between 0° C. and 150° C., more preferably at a temperature in the range from 20° C. to 100° C., and even more preferably in the range from 40° C. to 80° C. In an advantageous embodiment heat may be recovered from earlier steps of the process, for example by heat recovery from steps a) or b), which heat may be applied in step e).

In an especially preferred embodiment, cooling is applied in the caustic wash step b) by a heat-exchange with step e).

The separated organic phase, comprising the organic hydroperoxide, obtained in step (e), can advantageously be used in a process for the preparation of alkylene oxide according to the invention.

The alkene used in such a process is preferably an alkene comprising from 2 to 10 carbon atoms and more preferably an alkene comprising from 2 to 4 carbon atoms. The corresponding prepared alkylene oxide preferably also comprises from 2 to 10 carbon atoms and more preferably from 2 to 4 carbon atoms respectively. Examples of alkenes that can be used include ethene, propene, 1-butene and 2-butene, with which the corresponding ethylene oxide, propylene oxide and butylene oxides can be prepared.

The process according to the invention is especially advantageous for the preparation of propylene oxide. Hence, the most preferred alkene is propene, with which the corresponding propylene oxide can be prepared.

In an additional process step (f), at least part of an organic phase containing organic hydroperoxide, obtained from a process as described hereinabove, can contacted with an alkene to obtain an alkylene oxide. The organic hydroperoxide is converted into its corresponding alcohol. Preferably this reaction is carried out in the presence of a catalyst. A preferred catalyst for such process comprises titanium on silica and/or silicate. Further preferred catalysts are described in EP-A-345856. The reaction generally proceeds at moderate temperatures and pressures, in particular at temperatures in the range of from 25 to 200° C., preferably in the range from 40 to 135° C. The precise pressure is not critical as long as it suffices to maintain the reaction mixture as a liquid or as a mixture of vapour and liquid. In general, pressures can be in the range of from 1 to 100 bar, preferably in the range from 20 to 80 bar.

The alkylene oxide can be separated from the reaction product in any way known to be suitable to someone skilled in the art. For example, the liquid reaction product may be worked up by fractional distillation and/or selective extraction. The solvent, the catalyst and any unreacted alkene or hydroperoxide may be recycled for further utilization.

Preferably, the organic compound for use in the present invention is ethylbenzene, which is converted in step (f) into 1-phenyl-ethanol. If the organic compound is ethylbenzene such process generally further comprises:

(g) separating at least part of the 1-phenyl-ethanol from the reaction mixture obtained in step (f), and (h) converting the 1-phenyl-ethanol obtained in step g) into styrene.

Processes which can be used for this step have been described in WO 99/42425 and WO 99/42426. However, any suitable process known to someone skilled in the art can in principle be used.

The present invention is further illustrated by the following examples.

EXAMPLES 1-13

In a reactor, air was blown through ethylbenzene. The product obtained was concentrated such as to obtain a mixture containing about 26% wt of ethylbenzene hydroperoxide (EBHP) dissolved in ethylbenzene. Additionally, organic acid by-products, including about 66 ppmwt of formic and acetic acid, 72 ppmwt of propionic acid and 2843 ppmwt of benzoic acid, were present in this mixture.

The EBHP containing mixture was neutralized with an aqueous solution of about 0.5% wt of sodium hydroxide. Subsequently an organic phase and an aqueous phase were separated.

The obtained organic phase was contacted with an aqueous stream in a set-up as illustrated in FIG. 1. Organic phase (containing EBHP dissolved in ethylbenzene) (101) was contacted with an aqueous stream (102) and mixed in a static mixer (103). The mixture obtained from mixer (103) was fed into a horizontal separation vessel (104) comprising a coalescer bed (105) vertically arranged in the separation vessel, each coalescer bed containing E-type glass fibers with a diameter of 10 microns. In the separation vessel the mixture was separated in a purified organic phase stream (106) and an aqueous stream containing basic residue (107). Part of the aqueous stream was recycled (108) and part was removed from the set-up by an aqueous bleed (109). A make up was provided by a clean aqueous stream (110). The removal efficiency is determined by measuring the amount (ppmw based on the whole mixture) of sodium ($C_{Na}$) in the mixtures in respectively lines (101) and (106) by atomic adsorption spectroscopy, and calculating the efficiency according to the below formula I:

$$[C_{Na}(101)-C_{Na}(106)]/C_{Na}(101)*100 \qquad (I)$$

For each example, the inlet concentration (ppmw) of Na and the velocity of the mixture in line (101) is given in table 1. The removal efficiency has also been indicated in table 1.

In addition the weight ratio of organic phase (OR), aqueous phase (AQ) and make-up clean aqueous stream (CCC) used in each example; mass ratio of organic phase (OR) to aqueous phase (AQ); and the coalescer type is indicated in table 1. The aqueous phase was dispersed in the organic phase. The mean droplet size of the aqueous phase was determined by the method as described in Streiff et al. New Fundamentals for Liquid-Liquid Dispersion Using Static Mixers, MIXING IX, 1997. The results are indicated in table 1.

EXAMPLES 14-25

The same set-up and process conditions as specified in examples 1-13 were used. In this case, however, several different types of coalescer materials were used. The results are specified in table 2. The E-type glass fibers had a diameter of about 10 microns, whereas the Teflon fibers had a diameter of about 21 microns.

EXAMPLE 26

In a continuous process according to the present invention the following steps were carried out:

In a first caustic treatment step, a stream of 26% w/w ethylbenzene hydroperoxide dissolved in ethylbenzene (EBHP solution) containing 0.02 meq/g acids is contacted with an aqueous solution of about 0.5% w/w of NaOH at a temperature of 60-65° C.

Subsequently the organic phase and the aqueous phase are allowed to settle, during 14 minutes of settling time, in an empty horizontal vessel. The weight ratio of the EBHP solution to the aqueous solution was 0.22 upon contacting. The pH of the aqueous phase, exiting the empty horizontal vessel was about 8.

80% w/w of the separated aqueous phase comprising the aqueous NaOH solution was recycled to be contacted again with a fresh EBHP solution. The remaining 20% w/w was discharged as waste water and replenished with water from the below washing step and a fresh caustic solution comprising a 20% w/w NaOH dissolved in water. The organic phase, comprising the EBHP solution, leaving the vessel contained 59 ppmw sodium and the acid content is reduced to 0.003 meq/g.

In a second step, being a first washing step, a stream comprising the organic phase from the first step was mixed with a stream of wash water in a first static mixer creating a stream comprising a dispersion of water in the organic phase with a mean droplet size of 150 μm. The dispersion was fed into a first horizontal separation vessel. The mixture was evenly divided over a coalescer mat consisting of two layers of which one was a co-knit of stainless steel wire and fiberglass and the other was a co-knit of stainless steel wire and Teflon. Each layer had a thickness of 12 inch (30.5 cm) and together the two layers formed a 24 inch (61 cm) thick coalescer mat.

Subsequently the organic and aqueous phases were phase separated. The organic phase was led through a second coalescer mat consisting of two layers of which one was a co-knit of stainless steel wire and fiberglass and the other was a co-knit of stainless steel wire and Teflon. Each layer had a thickness of 12 inch (30.5 cm) and together the two layers formed a 24 inch (61 cm) thick coalescer mat.

90% w/w of the separated aqueous phase was recycled in a circulation stream to be contacted again with fresh organic phase in the first static mixer. The remaining 10% w/w of water to the first static mixer was re-plenished with a stream of wash water leaving a second horizontal separation vessel. The stream of organic phase leaving the first horizontal separation vessel contained 3.5 ppmw sodium.

In a third step, being a second washing step, the stream of organic phase from the previous washing step was mixed with a further stream of wash water in a second static mixer creating a stream comprising a dispersion of water in the organic phase with a mean droplet size of 150 μm. The dispersion was led onto a second horizontal separation vessel. The dispersed stream was evenly divided over a coalescer mat consisting of two layers of a co-knit of stainless steel wire and fiberglass. Each layer had a thickness of 12 inch (30.5 cm) and together the two layers formed a 24 inch (61 cm) thick coalescer mat.

The organic and aqueous phase were phase separated. The organic phase is led through a second coalescer mat consisting of two layers of a co-knit of stainless steel wire and fiberglass. Each layer had a thickness of 12 inch (30.5 cm) and together the two layers formed a 24 inch (61 cm) thick coalescer mat.

90% w/w of the separated aqueous phase was recycled in a circulation stream to be contacted again with fresh organic phase in the second static mixer, a stream of 10% w/w was recycled to the first static mixer of the second step. The remaining 10% w/w of water to the second static mixer was re-plenished with by a stream of fresh wash water. The weight phase ratio of organic phase to fresh water was 25.3:1.

The stream of organic phase leaving the second horizontal separation vessel contained 0.02 ppmw sodium.

The total effective acid removal of these subsequent steps was 85% and the sodium removal efficiency of the combined water wash steps was 99.97%.

TABLE 1

Examples 1 to 13

| Ex. | Inlet conc. Na (ppmw) | linear velocity(cm/s) | OR:AQ:CCC | AQ:OR ratio | droplet size | coalescer type | removal efficiency (%) |
|---|---|---|---|---|---|---|---|
| 1 | 23.6 | 0.86 | 400:50:15 | 1:10 | 43 | glass | 96.2 |
| 2 | 24.2 | 0.86 | 400:50:15 | 1:10 | 95 | glass | 97.1 |
| 3 | 24.9 | 0.86 | 400:50:15 | 1:10 | 200 | glass | 93.6 |
| 4 | 19.9 | 0.61 | 280:33:0 | 1:10 | 305 | glass | 88.6 |
| 5 | 18.8 | 0.47 | 220:30:0 | 1:10 | 406 | glass | 85.1 |
| 6 | 16 | 0.48 | 220:30:15 | 1:8 | 87 | glass | 91.1 |
| 7 | 26.2 | 0.48 | 220:30:15 | 1:8 | 191 | glass | 94.4 |
| 8 | 19.8 | 0.60 | 280:38:19 | 1:8 | 305 | glass | 91.4 |
| 9 | 21 | 0.48 | 220:30:15 | 1:8 | 405 | glass | 85.4 |
| 10 | 17.7 | 0.73 | 320:67:0 | 1:5 | 56 | glass | 96.9 |
| 11 | 19.6 | 0.73 | 320:67:12 | 1:5 | 122 | glass | 98.0 |
| 12 | 19.6 | 0.75 | 320:80:12 | 1:5 | 255 | glass | 97.9 |
| 13 | 23.3 | 0.65 | 280:63:12 | 1:5 | 300 | glass | 94.8 |

TABLE 2

Examples 14 to 25

| Ex. | Inlet conc. Na (ppmw) | linear velocity cm/s | OR:AQ:CCC | AQ:OR ratio | droplet size | coalescer type | removal efficiency (%) |
|---|---|---|---|---|---|---|---|
| 14 | 21.5 | 0.71 | 400:50:15 | 1:10 | 200 | glass | 93.6 |
| 15 | 28.1 | 0.86 | 330:40:15 | 1:10 | 251 | glass | 92.4 |
| 16 | 18.9 | 0.86 | 400:50 | 1:10 | 200 | SS/glass | 93.9 |
| 17 | 18.9 | 0.71 | 330:40 | 1:10 | 251 | SS/glass | 92.6 |
| 18 | 19.7 | 0.86 | 400:50 | 1:10 | 200 | Teflon/glass | 93.9 |
| 19 | 18.48 | 0.71 | 330:40 | 1:10 | 251 | Teflon/glass | 92.2 |
| 20* | 21.2 | 0.69 | 320:42 | 1:8 | 260 | Teflon | 85.8 |
| 21 | 19.4 | 0.69 | 320:42 | 1:8 | 260 | glass | 91.3 |
| 22* | 19.3 | 0.68 | 320:35 | 1:10 | 124 | Teflon | 89.4 |
| 23 | 22.4 | 0.68 | 320:35 | 1:10 | 124 | glass | 91.8 |
| 24* | 20.4 | 0.68 | 320:35 | 1:10 | 56 | Teflon | 90.1 |
| 25 | 18.8 | 0.68 | 320:35 | 1:10 | 56 | glass | 93.5 |

*comparative examples

EXAMPLE 27

Glass Fiber Corrosion

In order to establish the extent of corrosion of the glass fibers, E-type glass fibers were used in a first horizontal separation vessel in a first washing step as exemplified in example 26 for 4 months.

Figure 2A:
FIG. 2A us a photograph of glass fibers before use according to the present invention (fresh glass fibers)
Figure 2B:
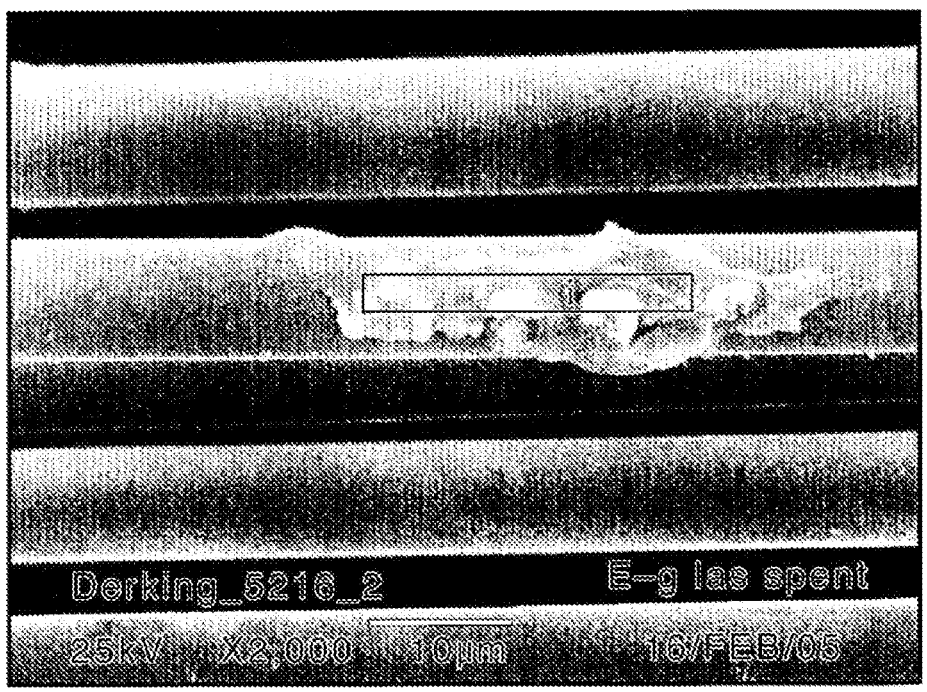
FIG. 2B is a photograph of glass fibers after use according to the present invention (spent glass fibers).

FIG. 2A shows glass fibers before use (fresh glass fibers) and FIG. 2B shows glass fibers after use (spent glass fibers). As can be seen, essentially no corrosion has taken place.

The invention claimed is:

1. A process for preparing an organic hydroperoxide, which process comprises:
   (a) oxidizing an organic compound to obtain an organic reaction product containing organic hydroperoxide;
   (b) mixing at least part of the organic reaction product of step (a) with a basic aqueous solution to obtain a mixture of basic aqueous solution and the organic reaction product;
   (c) separating the mixture of step (b) to obtain a separated organic phase containing organic hydroperoxide, and a separated aqueous phase;
   (d) mixing at least part of the separated organic phase of step (c) with water to obtain a mixture of an aqueous phase and the organic phase; and
   (e) separating the mixture of step (d) to obtain a separated organic phase containing organic hydroperoxide, and a separated aqueous phase;
   in which process the separation to a separated organic phase and a separated aqueous phase in step (e) is carried out with the help of a coalescer containing glass fibers.

2. A process according to claim 1 wherein the sequence of steps (d) and (e) is repeated one or more times.

3. A process according to claim 1, wherein the volume ratio of aqueous phase to organic phase in step (d) lies in the range from 1:100 to 1:2.

4. A process according to claim 1, wherein the mixture obtained in step d) is a dispersion comprising droplets having a Sauter mean droplet size in the range from 30 to 300 micrometers.

5. A process according to claim 1, wherein the glass fibers are glass fibers having a diameter in the range from 1 to 20 micrometers.

6. A process according to claim 1, wherein the mixing in step (d) is carried out by means of a static mixer.

* * * * *